United States Patent
Holdstock et al.

(10) Patent No.: US 7,645,846 B2
(45) Date of Patent: Jan. 12, 2010

(54) PROCESS FOR THE PREPARATION OF A DIOL

(75) Inventors: Barry Charles Holdstock, Surbiton (GB); Trevor Owen Glasey, Camberley (GB)

(73) Assignee: CooperVision International Holding Company LP, St. Michael (BB)

( * ) Notice: Subject to any disclaimer, the term of this patent is extended or adjusted under 35 U.S.C. 154(b) by 938 days.

(21) Appl. No.: 09/977,880

(22) Filed: Oct. 15, 2001

(65) Prior Publication Data

US 2002/0042549 A1    Apr. 11, 2002

Related U.S. Application Data

(63) Continuation-in-part of application No. PCT/GB00/00780, filed on Mar. 3, 2000.

(30) Foreign Application Priority Data

Apr. 16, 1999    (GB) .................................. 9908808.0

(51) Int. Cl.
C08F 24/00    (2006.01)
C08F 4/32    (2006.01)
C08F 18/00    (2006.01)

(52) U.S. Cl. .................. 526/273; 526/320; 526/230
(58) Field of Classification Search ................ 526/273, 526/320, 230
See application file for complete search history.

(56) References Cited

U.S. PATENT DOCUMENTS

| | | | | |
|---|---|---|---|---|
| 3,845,164 A | * | 10/1974 | Goto et al. | 525/81 |
| 4,056,496 A | * | 11/1977 | Mancini et al. | 523/106 |
| 4,413,038 A | | 11/1983 | Tobias | |
| 5,212,015 A | * | 5/1993 | Mitra et al. | 428/412 |
| 5,243,086 A | | 9/1993 | Jakobson | |
| 5,354,643 A | | 10/1994 | Cabrera | |
| 5,532,289 A | | 7/1996 | Benz | 523/106 |
| 6,239,298 B1 | * | 5/2001 | Williamson et al. | 554/117 |

FOREIGN PATENT DOCUMENTS

| | | |
|---|---|---|
| EP | 0039595 | 11/1981 |
| EP | 1171411 | 1/2005 |
| GB | 2097952 | 11/1982 |
| JP | 10-124533 | 5/1998 |
| WO | 00/63150 | 10/2000 |

OTHER PUBLICATIONS

Rohm and Haas, product data sheet on Amberjet product (Nov. 1998).*
G.M. Coppola, "Amberlyst-15, A Superior Acid Catalyst for the Cleavage of Acetals," Synthesis, No. 12, Dec. 1984, pp. 1021-1023.

* cited by examiner

Primary Examiner—William K Cheung
(74) Attorney, Agent, or Firm—Kilyk & Bowersox, P.L.L.C.

(57) ABSTRACT

There is provided a process for the preparation of a polymerizable composition comprising a cross-linker and a polymerizable monomer of formula (I) comprising (i) contacting a compound of formula (II) with an acid such as an imobilized acid; and (ii) neutralizing product of (i) such that a crosslinker is formed.

26 Claims, 2 Drawing Sheets

Variation in composition during stage 2

PROCESS FOR THE PREPARATION OF A DIOL

RELATED APPLICATIONS/INCORPORATION BY REFERENCE

This application is a continuation-in-part of PCT/GB00/00780, filed Mar. 3, 2000, designating the U.S., published Oct. 26, 2000 as WO 00/63150, and claiming priority from GB 9908808, filed Apr. 16, 1999. Mention is also made of PCT/GB00/00765, filed Mar. 3, 2000, designating the U.S., published Oct. 26, 2000 as WO 00/63149, and claiming priority from GB 9908806, filed Apr. 16, 1999. The foregoing applications, and more generally all documents cited herein (individually and collectively "application documents"), and all documents cited or referenced in the application documents (including documents cited during any prosecution of any patent applications, publications or patents), including any manufacturer's specifications, data sheets and the like for any commercially available products mentioned herein, are hereby incorporated herein by reference. The inventive entity of PCT/GB00/00765, WO 00/63149, and GB 9908806 is not another as to the inventive entity of the present application, and vice versa.

Also, it is noted that a polymerisable group or polymerisable monomer is a group or monomer having a suitable electron density, e.g., saturation or double and/or triple bond(s), such that the monomer or group is capable of polymerising, e.g., in the presence of an initiator such as a chemical initiator UV light.

The present invention relates to a process for the preparation of a diol. The diol may be used subsequently used as a monomer for the preparation of a polymeric device or material such as a hemocompatible coating, medical device, water soluble polymer material, paint, water borne coating or an ocular device (such as a contact lens).

Polymers made from polymerisable monomers have wide spread applications. For example, polymers are used as additives for coating applications, such as paints and adhesives. Polymers are also used to prepare lenses, such as contact lenses.

Polymers are prepared by polymerising one or more types of polymerisable monomers, such as by emulsion polymerisation, solution polymerisation, suspension polymerisation or bulk polymerisation. The monomer(s) may be polymerised in the presence of optional ingredients such as any one of emulsifiers, stabilisers, surface active agents, initiators (such as photoinitiators), inhibitors, dispersants, oxidising agents, reducing agents, viscosity modifiers, catalysts, binders, activators, accelerators, tackifiers, plasticizers, saponification agents, chain transfer agents, surfactants, fillers, dyes, metal salts, and solvents.

There are numerous references on polymerisation of polymerisable monomers. For example, some teachings may be found in "Emulsion Polymerization: Theory and Practice" by D. C. Blackley (published by Wiley in 1975) and "Emulsion Polymerization" by F. A. Bovey et al. (published by Interscience Publishers in 1965). For example, a polymer can be prepared from monomers such as methyl acrylate, ethyl acrylate, butyl acrylate, 2-ethylhexyl acrylate, decyl acrylate, methyl methacrylate, ethyl methacrylate, butyl methacrylate, styrene, butadiene, ethylene, vinyl acetate, vinyl esters, $C_9$, $C_{10}$ and $C_{11}$ tertiary monocarboxylic acids, vinyl chloride, vinyl pyridine, vinyl pyrrolidine, vinylidene chloride, acrylonitrile, chloroprene, acrylic acid, methacrylic acid, itaconic acid, maleic so acid and fumaric acid.

Examples of further teachings on polymerisation of polymerisable monomers may be found in "Vinyl and Related Polymers" by C. E. Schildknecht (New York: John Wiley & Sons 1952) and "Monomeric Acrylic Esters" by E. H. Riddle (New York: Reinhold Publishing Corp. 1954). and by A. G. Alexander (J Oil Colour Chemists' Association [1962] 45 12) and G. G. Greth and J. E. Wilson (J Appl Polymer Sci [1961] 5 135).

More recent teachings regarding polymerisation methods may be found in EP-A-0622378, EP-A-0634428, EP-A-0623632, EP-A-0635522, EP-A-0633273, EP-A-0632157, EP-A-0630908. EP-A-0630641, EP-A-0628614, EP-A-0628610, EP-A-0622449, EP-A-0626430 and EP-A-0625529.

As mentioned above, one particular application of polymers is in the preparation of lenses. especially contact lenses or intraocular lenses. Examples of teachings for the preparation of contact lenses may be found in EP-A-0359539, which discloses a method of forming a soft contact lens. Other documents that describe the preparation of contact lenses include WO-A-9502617 which discloses a contact lens made from a vinyl polymer bearing phosphonium groups, JP-A-063 13009 which discloses a contact lens made from a polymer having a terminal phosphoryl-choline group, WO-A-9429756 which discloses a gas permeable ocular lens made from a block copolymer and a second polymer component. WO-A-9409042 which discloses a contact lens comprising polymer and a UV absorbing constituent, and WO-A-9211407 which discloses a tinted contact lens comprising a polymer and a dye wherein the lens is prepared by incorporating a dye into a hydrophilic polymer while the polymer is being formed. Further documents describing preparing contact lenses and the like from polymerisable monomers include EP-A-0574352. EP-A-0439394, EP-A-0378511 and EP-A-0424520.

Whilst polymers can be fairly easily prepared from polymerisable monomers there can be a problem in reliably and cheaply obtaining suitable monomers in a satisfactory pure form. In this regard, many desired polymerisable monomers are supplied with impurities. These impurities can be detrimental to the final product.

Impurities which are particularly problematic are compounds which act as cross-liners during the polymerisation of the monomer. Whilst the presence of cross-linkers is often required during the polymerisation of a monomer, the presence of impurities which act as cross-linkers may cause at least two problems. Firstly, to achieve a desired degree of cross-linking during polymerisation, the addition of further cross-linker is often required. However, if the amount of cross-linker impurity present in the monomer is not known, the required amount of additional cross-linker cannot be readily calculated. Thus, controlling the degree of cross-linking may be difficult. Moreover, if cross-linker is present in an amount grater then is necessary to provide the required degree of cross-linking, cross-linker must be removed prior to polymerisation.

An example of a monomer in which impurities, in particular cross-linkers, are a problem is glyceryl methacrylate (GMA) which is a preferred monomer for preparing contact lenses. Examples of documents mentioning the use of such a monomer include U.S. Pat. No. 5,236,969, JP-A-04335007, GB-A-2180243 and EP-A-0100381. There are two major problems with GMA. First, the impurities often vary from batch to batch and so make it difficult to have a standard purification protocol. Second. GMA is a very expensive monomer.

There have been attempts to prepare GMA from other monomers, such as isopropylideneglyceryl methacrylate (IP-GMA) [i.e. 2,2-dimethyl-1,3-dioxolan-4-yl methyl methacrylate (GMAK)]. One such process for preparing GMA is disclosed in U.S. Pat. No. 4,056,496 wherein the process includes reacting IPGMA with sulphuric acid and hydroquinone for a period of 16 hours.

Another process for preparing GMA, also mentioned in U.S. Pat. No. 4,056,496, includes the hydrolysis of glycidyl methacrylate (GYMA) by treating GYMA with concentrated sulphuric acid for 6 days (M. F. Refojo [1965] Journal of Polymer Science 9 pp 3161-3170). This process is particularly disadvantageous because glycidyl methacrylate is highly toxic and carcinogenic. Moreover, glycidyl methacrylate is a cross-linker and further cross-linkers are formed during the reaction (particularly by the reaction of glycidyl methacrylate with GMA in the presence of acid). The presence of these cross-linkers may require further purification steps or may be detrimental to any polymer prepared by polymerisation of the obtained monomer. Yet further the process of Refojo requires neutralisation of $H_2SO_4$ with $Ba(OH)_2$ and extraction with a toxic flammable solvent.

The distillation of GMA to prepare purified GMA followed by addition of cross-linker is also practised in the art. Distillation is however both difficult and costly. GMA is high boiling and therefore costs of distillation are high. Distillation typically gives losses of 15-20% of the product to be purified. Moreover, GMA may polymerise during distillation and valuable monomer lost. Yet further, the equipment which may be required to perform the distillation e.g. falling film evaporator, is expensive.

Clearly these prior art methods do not provide suitable control of the amount of cross-linker present in the monomer and therefore do not allow for control of the degree of cross-linking during polymerisation. The monomers obtained by the prior art may contain too much cross-linker for some applications or require expensive and difficult purification. Moreover, the prior art methods which attempt to provide pure monomer or to provide monomer comprising cross-linker are very labour intensive and include the use of hazardous chemicals, including toxic chemicals and flammable solvents, and hazardous process steps.

Further prior art methods for preparing GMA polymers are disclosed in U.S. Pat. No. 4,338,419, FR 8207595, WO 93/0841 and Ezrielev et al, Vysokomol. Soedin. Ser. B. 20(10), 777-9, Hild, Makromol. Chem. 177, 1947-1972 (1976) and Beinert et al. Die Makromolekulare Chemie, 175, 2069-2077 (1974).

U.S. Pat. No. 5,532,289 discloses a process for forming a soft contact lens. According to the claims of this patent the lens is formed from a copolymer consisting essentially of 2,3-dihydroxypropyl methacrylate (GMA) and 2-hydroxyethyl methacrylate. Hydroxyethyl methacrylate is sometimes referred to as HEMA. The process of U.S. Pat. No. 5,532,289 requires a pre-distillation step wherein GMA is distilled. Hence, the process of U.S. Pat. No. 5,532,289 is laborious and costly.

WO 98/07055 discloses a process of preparing an ocular device (such as a contact lens) consisting essentially of GMA and HEMA, the process comprising the following steps: a) copolymerising a second monomer and a first monomer having attached to it a modifier group, thereby to form a first polymer having associated with it the modifier group: and b) modifying all or some the modifier group associated with the first polymer to form a second polymer different from the first polymer thereby to form the ocular device consisting essentially of GMA and HEMA.

The present invention seeks to overcome the problems associated with the known processes for preparing polymers.

According to a first aspect of the present invention there is provided a process for the preparation of a polymerisable composition comprising a cross-linker and a polymerisable monomer of formula I comprising the steps of:
(i) contacting a compound of formula II with an immobilised acid.

wherein X, Y, Z, $R^1$, P and Q are independently selected from a hydrocarbyl group or hydrogen and wherein A is $(CH_2)_n$ wherein n is 0 or 1, (ii) neutralising the product of step (i) such that the cross-linker is formed.

According to a second aspect of the present invention there is provided an ocular device (such as a contact lens) prepared by the process according to the present invention.

By the term "cross-linker" we mean a compound which increases the degree of cross-linking of a monomer during polymerisation when compared to the polymerisation of the monomer in the absence of the cross-linker.

The present invention may provide a number of advantages.

The present invention may allow for the amount of cross-linker present in the composition to be controlled. Thus, the present invention provides a composition comprising a polymerisable monomer wherein the degree and/or rate of cross-linking of the polymerisable monomer may be controlled. Moreover, the concentration of cross-linker may be controlled such that further additions of cross-linker are possible to achieve the desired/optimum degree and/or rate of cross-linking during polymerisation.

The present invention has the advantage that because of the low initial cross-linker concentration in the monomer, controlled additions of further cross-linker to achieve the desired/optimum level are possible. In contrast if monomer e.g. GMA, in accordance with the prior art is used, the level of cross-linker is often already too high to allow further additions without detriment to the mechanical properties of the final polymer, such as a lens.

It will be appreciated by a person skilled in the art that at least one of X, Y, Z or $R^1$ is a polymerisable group such that the compound of formula I is a polymerisable monomer. In a preferred aspect, $R^1$ is a polymerisable group.

In a preferred aspect of the process of the present invention the acid is a strong acid. By the term "strong acid" it is meant an acid having a pKa of less than 3.

In a preferred aspect of the process of the present invention the acid is immobilised on an ion exchange resin. Preferably the ion exchange resin is Amberlyst 15. obtainable from Röhm and Haas.

In a preferred aspect of the process of the present invention, the product of step (i) is neutralised by contacting the product with an immobilised alkali. Preferably the immobilised alkali is an immobilised hydroxide. More preferably the immobilised hydroxide is Amberjet 4400 (OH) obtainable from Röhm and Haas.

As mentioned above, preferably $R^1$ is a polymerisable group. Preferably, $R^1$ is selected from hydrocarbyl group, and hydrocarbyl esters, preferably unsaturated hydrocarbyl esters.

The term "hydrocarbyl group" as used herein means a group comprising at least C and H and may optionally comprise one or more other suitable substituents. Examples of such substituents may include halo-, alkoxy-, nitro-, hydroxy, carboxyl, epoxy, acrylic, hydrocarbon, N-acyl, or cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen.

The term "hydrocarbyl ester" as used herein means a hydrocarbyl group comprising a —C(O)—O— group.

The term "unsaturated hydrocarbyl ester" as used herein means a hydrocarbyl ester comprising at least one carbon-carbon double bond or at least one carbon-carbon triple bond.

Preferably, the hydrocarbyl group is a linear or a branched group. The branched group may contain one or more branches.

In one aspect, the linear or a branched hydrocarbyl group may contain from 1 to 20 carbon atoms, from 1 to 15 carbon atoms, from 1 to 10 carbon atoms, from 1 to 5 carbon atoms, or from 1 to 3 carbon atoms.

The linear or a branched hydrocarbyl group may be saturated or unsaturated. In one aspect the linear or a branched hydrocarbyl group may saturated.

Preferably, the hydrocarbyl group comprises an alkyl backbone. The backbone may be interrupted by one or more non-alkyl groups. The non-alkyl groups may be selected from ester, ether and combinations thereof.

In one aspect, the alkyl backbone may contain from 1 to 20 carbon atoms, from 1 to 15 carbon atoms, from 1 to 10 carbon atoms, from 1 to 5 carbon atoms, or from 1 to 3 carbon atoms.

The alkyl backbone may contain one or more alkyl groups branched from the alkyl backbone. In one aspect, each alkyl branch may contain from 1 to 20 carbon atoms, from 1 to 15 carbon atoms, from 1 to 10 carbon atoms, from 1 to 5 carbon atoms, or from 1 to 3 carbon atoms.

The hydrocarbyl group may be a cyclic group. In this regard, the hydrocarbyl group can be a single ring group or a polycyclic group. Here, the term "polycyclic" includes fused and non-fused ring structures including combinations thereof.

At least one of the cyclic groups of the polycyclic group may be a heterocyclic group (a heterocycle) or a non-heterocyclic group.

The cyclic group or at least one of the cyclic groups of the polycyclic group may be a saturated ring structure or an unsaturated ring structure (such as an aryl group).

The hydrocarbyl group may contain any one or more of C, H, O, Si, N, P, halogen (including Cl, Br and I), S and P. In the preferred aspect wherein the hydrocarbyl group comprises an alkyl backbone, the alkyl backbone may be interrupted by one or more of any one or more of C, H, O, Si, N, P, halogen (including Cl, Br and I), S and P.

Preferably, the hydrocarbyl group is a hydrocarbon group.

Here the term "hydrocarbon group" means any one of an alkyl group, an alkenyl group, an alkynyl group, an acyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

The hydrocarbon group may have from 1 to 20 carbon atoms, from 1 to 15 carbon atoms, from 1 to 10 carbon atoms, from 1 to 5 carbon atoms, or from 1 to 3 carbon atoms.

In a preferred embodiment $R^1$ is a group of formula III (III)

wherein $R^2$ is selected from methyl, ethyl, propyl and butyl and $R^3$ is selected from an unsaturated $C_{1-5}$ alkyl. In a highly preferred embodiment $R^2$ is $CH_3$ and $R^3$ is =$CH_2$.

Preferably, X, Y, P and Q of formulae given in the present specification are independently selected from a hydrocarbyl group and hydrogen. Preferably, the hydrocarbyl group is a hydrocarbon group. More preferably the hydrocarbyl group is a hydrocarbon group having from 1 to 20 carbons. Yet more preferable, the hydrocarbyl group is selected from methyl, ethyl, propyl and butyl.

In a highly preferred embodiment X is H, Y is H, Z is H, n=0, P is $CH_3$, Q is $CH_3$ and $R^1$ is a group of formula III, in which $R^2$ is $CH_3$ and $R^3$ is =$CH_2$.

When a compound of formula II is contacted with an immobilised acid to provide a polymerisable monomer of formula I, an acid is formed as a by-product during the reaction. For example, when 2,2-dimethyl-1,3-dioxolan-4-yl methyl methacrylate (GMAK) is contacted with an immobilised acid to provide GMA, methacrylic acid is formed albeit in a low concentration. In a preferred aspect of the present invention, the acid is neutralised in step (ii) such that a cross-linker is formed, wherein the cross-linker is glycerol dimethacrylate (DGMA).

Thus in a highly preferred aspect the present invention provides a process for the preparation of a polymerisable composition comprising a cross-linker and a polymerisable monomer of formula I

(I)

comprising the steps of
(i) contacting a compound of formula II (II)

with an immobilised acid,
wherein X is H
Y is H
Z is H
A is $(CH_2)_0$
P is $CH_3$
Q is $CH_3$
and wherein $R^1$ is a group of formula III (III)

in which $R^2$ is $CH_3$ and $R^3$ is $=CH_2$;
(ii) neutralising the product of step (i) by contacting the product with an immobilised hydroxide such that the cross-linker is formed, wherein the cross-linker is glycerol dimethacrylate.

In other words, in a highly preferred aspect, the present invention provides a process for the preparation of a composition comprising glyceryl methacrylate (GMA), and glycerol dimethacrylate comprising the steps of (i) contacting (2,2-dimethyl-1,3-dioxolan-4-yl) methyl methacrylate (GMAK) with an immobilised acid, (ii) neutralising the product of step (i) by contacting the product with an immobilised hydroxide such that the glycerol dimethacrylate is formed.

In a preferred embodiment of the present invention the immobilised acid is contacted with the compound of formula II in the presence of water.

In a preferred embodiment of the present invention the process further comprises providing means for containing the immobilised acid, contacting the immobilised acid with the compound of formula II and passing a gas through the immobilised acid. In this preferred aspect of the present invention extremely high conversions have been achieved. When GMAK was contacted with immobilised acid a conversion of >99.9% was achieved.

Preferably the gas contains oxygen. More preferably, the gas is air.

Preferably the means for containing the immobilised acid comprises a fluidised bed reactor.

In a further preferred aspect of the present invention the process comprises extracting the gas from the means for containing the immobilised acid after the gas has passed through the immobilised acid. The extracted gas may contain a reaction product of the contact of the compound of formula II with the immobilised acid. The reaction product may be of the formula P—C(O)—Q. By removing the reaction product, the equilibrium II≈I+P—C(O)—Q will be driven towards I.

Thus the rate of conversion and/or ultimate conversion of I will be increased and, in a preferred aspect, essentially quantitative conversion may be achieved.

It will be appreciated that reaction product P—C(O)—Q is a volatile compound. By the term "volatile compound" we mean that the compound has a boiling point of less than 150° C. and/or is capable of forming an azeotrope with water.

Thus, in one preferred aspect of the present invention the compound of formula II is or is part of a polymer. However, as explained above, the compound of formula II is preferably a monomer.

In a preferred aspect the process of the present invention further comprises the step of polymerising the polymerisable composition to provide a medical device, in particular an ocular device such as a contact lens.

The present invention is very advantageous for preparing ocular devices, such as contact lenses (both hard and soft contact lenses), intraocular lenses, interocular lenses and intercorneal implants, as well as prostheses and hydrogel articles. In this regards the present invention not only enables the ocular devices to be made more easily but also it allows, by providing a greater choice of possible degrees and/or rates of cross-linking, greater control over any one of the shrinkage, the dimensional consistency the swell, the water sensitivity, the hydrophobicity or the hydrophilicity, or combinations thereof, of the resultant polymer.

The medical device and/or polymerisable composition may also comprise conventional additional components such as any one or more of emulsifiers, stabilisers, surface active agents, initiators (such as photoinitiators), inhibitors, dispersants, oxidising agents, reducing agents, viscosity modifiers, catalysts, binders, activators, accelerators, tackifiers, plasticizers, saponification agents, chain transfer agents, cross-linking agents, surfactants, fillers, dyes, metal salts, and solvents.

By way of example, the surfactants and dispersants can be salts of fatty rosin and naphthenic acids, condensation products of naphthalene sulphonic acid and formaldehyde of low molecular weight, carboxylic polymers and copolymers of the appropriate hydrophile-lipophile balance, higher alkyl sulfates, such as sodium lauryl sulfate, alkyl aryl sulfonates, such as dodecylbenzene sulfonate, sodium or potassium isopropylbenzene sulfonates or isopropylnaphthalene sulfonates; sulfosuccinates, such as sodium dioctylsulfosuccinate alkali metal higher alkyl sulfosuccinates, e.g. sodium octyl sulfosuccinate, sodium N-methyl-N-palmitoyl-taurate, sodium oleyl isethionate, alkali metal salts of alkylarylpolyethoxyethanol sulfates or sulfonates, e.g. sodium t-octylphenoxy-polyethoxyethyl sulfate having 1 to 5 oxyethylene units. Typical polymerisation inhibitors that can be used include hydroquinone, monomethyl ether, benzoquinone, phenothiazine and methylene blue.

In a preferred embodiment the dye is selected from the group consisting of 2-hydroxybenzophenone, oxidiazoles, salicylic acid, resorcinol monobenzoate, benzotriazole, preferably 2H-benzotriazole, benzothiazoloazine, preferably 2N-benzothi-azoloazine, α-cyano-β-phenylcinnainic acid, polyalkypiperidine and derivatives thereof.

Preferably, the dye is selected from benzotriazole, in particular 2H-benzotriazole and derivatives thereof.

The composition and/or medical device of the present invention may comprise one or more additional comonomers. Examples of the one or more additional comonomers that can be used in the present invention include one of: (alkyl and cycloalkyl) acrylates: (alklyl and cycloalkyl) methacrylates; free-radical polymerisable olefinic acids, including alkoxy-, alkylphenoxy-, alkylphenoxy-(polyethyleneoxide)-, vinyl ester-, amine substituted (including quaternary ammonium salts thereof), nitrile-, halo-, hydroxy-, and acid substituted (for example phospho- or sulpho-) derivatives thereof; and other suitable ethylenically unsaturated polymerisable moieties: including combinations thereof. Preferably the alkyl and cycloalkyl groups contain up to 20 carbon atoms. e.g. ($C_1$-$C_{20}$ alkyl and $C_1$-$C_{20}$ cycloalkyl) acrylates, and ($C_1$-$C_{20}$ alkyl and $C_1$-$C_{20}$ cycloalkyl) methacrylates. In more detail, typical comonomers include any one of methyl acrylate, ethyl acrylate, n-propyl acrylate, isopropyl acrylate, n-butyl acrylate, isobutyl acrylate, t-butyl acrylate, isobornyl acrylate, pentyl acrylate, hexyl acrylate, octyl acrylate, iso-octyl acrylate, nonyl acrylate, lauryl acrylate, stearyl acrylate, eicosyl acrylate, 2-ethylhexyl acrylate, cyclohexyl acrylate, cycloheptyl acrylate, methyl methacrylate, ethyl methacrylate, hydroxymethylacrylate, hydroxymethylmethacrylate, propyl methacrylate, n-butyl methacrylate, t-butyl methacrylate, isobutyl methacrylate, pentyl methacrylate, hexyl methacrylate, cyclohexyl methacrylate, 2-ethylhexyl methacrylate, isobornyl methacrylate, heptyl methacrylate, cycloheptyl methacrylate, octyl methacrylate, iso-octyl methacrylate, nonyl methacrylate, decyl methacrylate, lauryl methacrylate, eicosyl methacrylate, dodecyl acrylate, pentadecyl acrylate, cetyl acrylate, stearyl acrylate, eicosyl acrylate, isodecyl acrylate, vinyl stearate, nonylphenoxy-(ethyleneoxide)$_{1-20}$ acrylate, octadecene, hexadecene, tetradecene, dodecene, dodecyl methacrylate, pentadecyl methacrylate, cetyl methacrylate, stearyl methacrylate, eicosyl methacrylate, isodecyl methacrylate, nonylphenoxy-(ethyleneoxide)$_{1-20}$ methacrylate, acrylic acid, methacrylic acid, fumaric acid, crotonic acid, itaconic acid, fumaric anhydride, crotonic anhydride, itaconic anhydride, maleic acid, maleic anhydride, styrene, alpha-methyl styrene, vinyl toluene, acrylonitrile, methacrylonitrile, ethylene, vinyl acetate, vinyl chloride, vinylidene chloride, acrylamide, methacrylamide, methacrylamide 2-cyanoethyl acrylate, 2-cyanoethyl methacrylate, dimethylaminoethyl methacrylate, dimethylamninopropyl methacrylate t-butylaminoethyl methacrylate, glycidyl acrylate, glycidyl methacrylate, glyceryl acrylate, glyceryl methacrylate, benzyl acrylate, benzyl methacrylate, phenyl acrylate, phenyl methacrylate, vinyl pyridine, vinyl pyrrolidine, siloxanes, silanes and mixtures thereof. Other polymerisable monomers are disclosed in U.S. Pat. No. 2,879,178. U.S. Pat. No. 3,037,006. U.S. Pat. No. 3,502,627, U.S. Pat. No. 3,037,969 and U.S. Pat. No. 3,497,485.

Preferred comonomers include any one of glyceryl methacrylate (GMA), (2,2 dimethyl-1,3-dioxolan4-yl) methyl methacrylate (GMAK), hydroxy ethyl methacrylate (HEMA), methacrylic acid, acrylic acid, GYMA, N-vinyl pyrrolidone, alkyl methacrylates (such as $C_{1-20}$ alkyl methacrylates, more preferably $C_{1-15}$ alkyl methacrylates, more preferably $C_{1-10}$ alkyl methacrylates, more preferably $C_{1-5}$ alkyl methacrylates, such as methyl methacrylate), alkyl acrylates (such as $C_{1-20}$ alkyl acrylates, more preferably $C_{1-5}$ alkyl acrylates, more preferably $C_{1-10}$ alkyl acrylates, more preferably $C_{1-5}$ alkyl acrylates, such as methyl acrylate), aryl methacrylates, aryl acrylates, diacetone acrylamide, acrylamide, methacrylamide, N-alkyl acrylamides (such as $C_{1-20}$ N-alkyl acrylamides, more preferably $C_{1-15}$ N-alkyl acrylamides, more preferably $C_{1-10}$ N-alkyl acrylamides, more preferably $C_{1-5}$ N-alkyl acrylamides, such as methyl acrylamide), N-alkyl methacrylamides (such as $C_{1-20}$ N-alkyl methacrylamides, more preferably $C_{1-15}$ N-alkyl methacrylamides, more preferably $C_{1-10}$ N-alkyl methacrylamides, more preferably $C_{1-5}$ N-alkyl methacrylamides, such as methyl methacrylamide), vinyl acetate, vinyl esters, styrene, other substituted olefins, N-dialkyl acrylamides (such as $C_{1-20}$ N-dialkyl acrylamides, more preferably $C_{1-15}$ N-dialkyl acrylamides, more preferably $C_{1-10}$ N-dialkyl acrylamides, more preferably $C_{1-5}$ N-dialkyl acrylamides, such as N N dimethyl acrylamide), N-dialkyl methacrylamides (such as $C_{1-20}$ N-dialkyl methacrylamides, more preferably $C_{1-15}$ N-dialkyl methacrylamides, more preferably $C_{1-10}$ N-dialkyl methacrylamides, more preferably $C_{1-5}$ N-dialkyl methacrylamides, such as N N dimethyl methacrylamide), 3-methacryloxypropyl tris (trimethysilyl siloxy) silane (TRIS monomer), fluoro substituted alkyl and aryl acrylates and methacrylates (preferably wherein the alkyl is $C_{1-20}$ alkyl, more preferably $C_{1-15}$ alkyl, more preferably $C_{1-10}$ alkyl, more preferably $C_{1-5}$ alkyl), and combinations thereof.

More preferred comonomers include any one of glyceryl methacrylate (GMA), (2,2 dimethyl-1,3-dioxolan-1-yl) methyl methacrylate (GMAK), 2-hydroxy ethyl methacrylate (2-HEMA), methacrylic acid, acrylic acid and glycidyl methacrylate, or combinations thereof.

The lists of comonomers also include substituted derivatives of those monomers, such as halogenated monomers, especially fluorinated monomer derivatives, and acetal and ketal derivatives.

The polymerisable monomer of the composition of the present invention and the one or more additional comonomers may be selected so that the composition and/or ocular device of the present invention consists essentially of GMA and HEMA.

In a preferred aspect the present invention also provides an ocular device (such as a contact lens) obtained by the process of the present invention wherein the ocular device comprises HEMA in amounts of from 80-20%; GMA in amounts of from 20-80% by weight; and optionally a cross-linking polymerised monomer in an amount of 5% or less; and wherein the ocular device contains less than 0.01% methacrylic acid.

In a preferred aspect of the present invention the compound of formula II is a derivative of GMA such as (2,2-dimethyl-1,3-dioxolan-4-yl) methyl methacrylate (GMAK). GMAK can be prepared following the teachings of Mori et al ([1994] Macromolecules 27 pp 35-39) and Oguchi et al Polym Eng. Sci. ([1990] 30 449). This preferred process of the present invention is also of particular interest as GMAK can be readily synthesised from cheap, commercially available materials and it can be prepared in a pure state, i.e. free from the substances normally present in commercial GMA, especially cross-linking substances.

In a preferred aspect the process of the present invention comprises the step of polymerising the polymerisable monomer of formula I. Any typical, suitable polymerisation method may be used. The preferred method is free radical polymerisation, thermal or UV initiated.

A polymer prepared in accordance with the present invention may be fabricated as buttons or cast moulded or spun cast lenses.

The invention will now be described, by way of example only, with reference to the accompanying drawings in which.

EXAMPLES

1. Conversion of GMAK To Glycerine Methacrylate (GMA)

The method involves the acid catalysed hydrolysis of the ketal (GMAK) with a strong acid cation exchange resin.

Reagents Employed

| | |
|---|---|
| GMAK (washed) | 2880 ml |
| Deionised water | 921 ml |
| Amberlyst 15 (wet) cation exchange resin | 288 g |

GMAK was obtained was prepared by transesterification of methyl methacrylate and Solketal (2,2-dimethyl-4-hydroxymethyl-1,3-dioxolane).

Before use the Amberlyst 15 (wet) was repeatably washed with deionised water to remove acidic impurities.

3000 ml of GMAK is washed with its own volume of deionised water to remove any Solketal. If the GMAK contains a high concentration of Solketal separation will be difficult.

The reagents are placed in a 5 liter bottle and a stream (11 liter/min) of filtered air of ambient temperature (15 to 18° C.) passed through the mixture for 48 hours.

The cation exchange resin is then filtered off using a Buchner funnel and flask.

288 g of well washed Amberjet 4400 (OH) anion exchange resin is added to the filtrate and stirred for one hour to neutralise the methacrylic acid. The resin is then filtered off using a Buchner funnel and flask.

The filtrate is transferred to a 2 liter amber glass bottle and a rapid stream of dry filtered air passed through to reduce the water content to <3%. 50 ppm of methyl ether of hydroquinone is added as an inhibitor.

Figure 1:
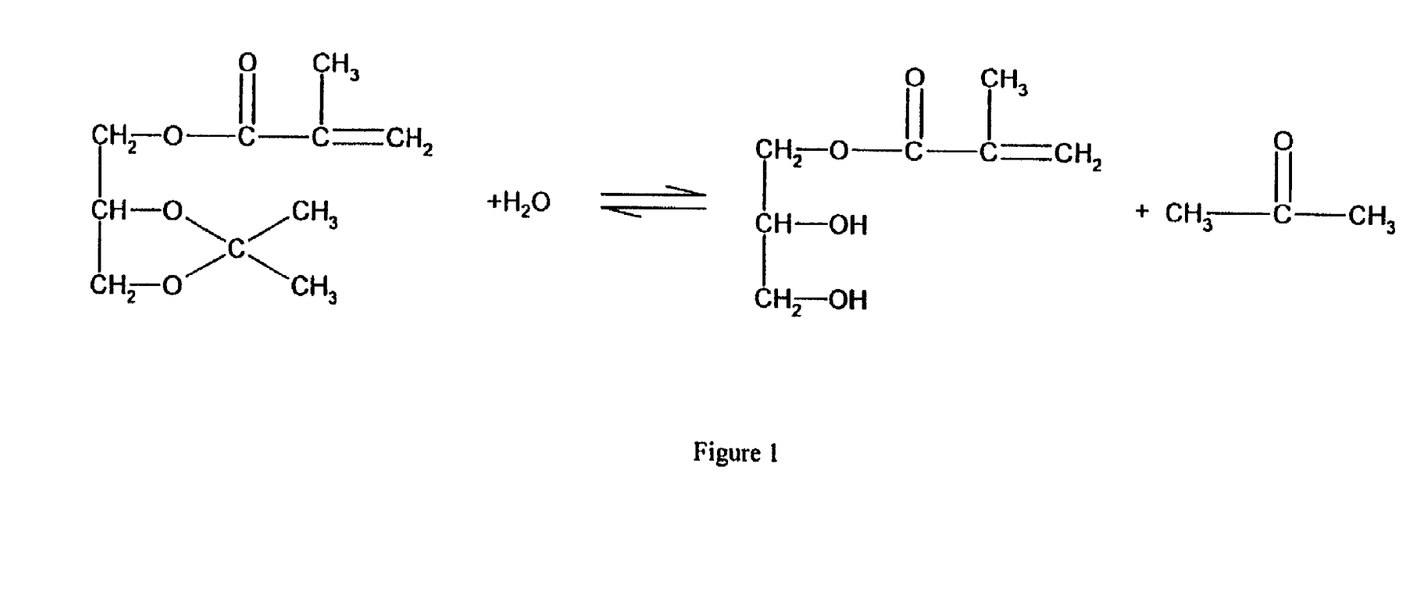
FIG. 1 shows a reaction scheme of a preferred process in accordance with the present invention.
Figure 2:
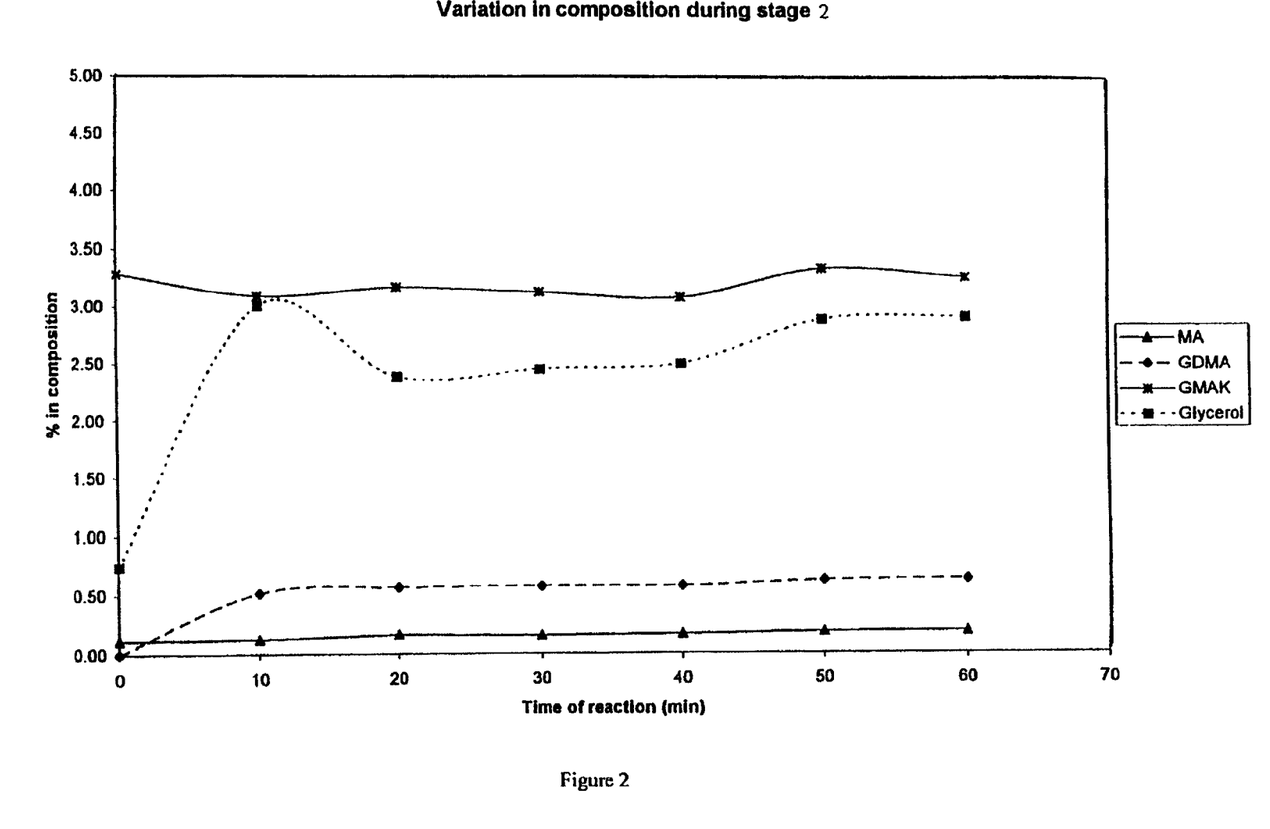
FIG. 2 shows a graph.

A yield of 1860 g of GMA was obtained. The cross-linker content was 0.8% glyceryl methacrylate. Details of samples analysed by UV and RI detection are given below. The data are also illustrated in FIG. 2.

2. Cast Moulding 10 g of GMA (prepared in Example 1) was blended with 10 g o10 g of HEMA. Azo-isobutyronitrile (AIBN) (0.2%) was dissolved in the mixture which was then filtered. The mixture was charged into polypropylene moulds which were assembled and heated to 120° C. for 30 minutes. The cured lenses were ejected and equilibrated in saline solution. The resulting hydrogel lenses had a water content of 60%.

3. Spin Casting 10 g of GMA (prepared in Example 1) was blended with 10 g of HEMA. Benzoir methyl ether (0.2%) was dissolved in the mixture which was then filtered. The mixture was charged into PVC moulds designed for spin casting. After passage through a bank of UV lamps the cured lenses were removed from the moulds by exposure to warm water and then equilibrated in saline.

4. Buttons

10 g of GMA (prepared in Example 1) was blended with 10 g of HEMA. Isopropyl per dicarbonate (0.1%) was dissolved in the mixture which was then filtered. The mixture was charged into polypropylene button moulds which were sealed and immersed in a water bath. After 16 hours at 32° C. the clear colourless buttons were ejected and heated to 120° C. for 1 hour and allowed to cool to 50° C. at a rate of 17° C./hr. Lenses were cut from the buttons and equilibrated in saline.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention shall be further described in the following numbered paragraphs:

1. A process for the preparation of a polymerisable composition comprising a cross-linker and a polymerisable monomer of formula I

| | Composition by UV Detector (%) | | | | Composition by RI Detector (%) | | | |
|---|---|---|---|---|---|---|---|---|
| Sample | GMA | MEHQ | GDMA | GMAK | Glycerol | GMA | GDMA | GMAK |
| 1 | 99.37 | 0.04 | 0.84 | 0.11 | 3.02 | 99.11 | 0.67 | 0.00 |
| 2 | 95.12 | 0.04 | 2.25 | 0.05 | 3.03 | 95.30 | 2.01 | 0.00 |
| 3 | 98.00 | 0.04 | 1.59 | 0.01 | 2.59 | 97.95 | 1.41 | 0.00 |
| 4 | 97.41 | 0.04 | 1.41 | 0.05 | 3.40 | 97.23 | 1.29 | 0.00 |
| 5 | 94.13 | 0.03 | 1.41 | 2.26 | 3.02 | 94.15 | 1.24 | 2.18 |
| 6 | 94.08 | 0.05 | 1.35 | 2.02 | 3.00 | 93.84 | 1.14 | 1.81 |
| 7 | 100.11 | 0.05 | 1.38 | 0.01 | 2.60 | 100.80 | 1.16 | 0.00 |
| 8 | 92.98 | 0.04 | 1.44 | 0.01 | 2.69 | 93.53 | 1.34 | 0.00 |
| 9 | 99.39 | 0.04 | 1.57 | 0.38 | 1.63 | 99.39 | 1.42 | 0.00 |
| 10 | 91.89 | 0.03 | 1.40 | 0.06 | 3.14 | 91.94 | 1.06 | 0.00 |
| 11 | 95.11 | 0.04 | 1.41 | 0.39 | 3.09 | 94.30 | 1.23 | 0.00 |
| 12 | 97.58 | 0.04 | 1.29 | 0.04 | 3.64 | 98.04 | 1.06 | 0.00 |
| 13 | 97.77 | 0.04 | 1.45 | 0.04 | 3.23 | 96.96 | 1.24 | 0.00 |
| 14 | 97.73 | 0.05 | 1.58 | 0.59 | 2.80 | 98.04 | 1.40 | 0.47 |
| Mean | 96.48 | 0.04 | 1.46 | 0.43 | 2.92 | 96.47 | 1.26 | 0.32 |
| St Dev | 2.57 | 0.00 | 0.29 | 0.75 | 0.47 | 2.63 | 0.29 | 0.72 | comprising the steps of:
(i) contacting a compound of formula II with an immobilised acid,
wherein X, Y, Z, $R^1$, P and Q are independently selected from a hydrocarbyl group or hydrogen and wherein A is $(CH_2)_n$, wherein n is 0 or 1;
(ii) neutralising the product of step (i) such that the cross-linker is formed.

2. A process according to paragraph 1 wherein the acid is a strong acid.

3. A process according to paragraph 1 or 2 wherein the acid is immobilised on an ion exchange resin.

4. A process according to any one of the preceding paragraphs wherein X and Y are independently selected from hydrocarbon groups having from 1 to 20 carbon atoms and hydrogen.

5. A process according to any one of the preceding paragraphs wherein R1 is selected from hydrocarbon groups having from 1 to 20 carbon atoms, and hydrocarbyl esters, preferably unsaturated hydrocarbyl esters.

6. A process according to any one the preceding paragraphs wherein $R^1$ is a group of formula III wherein $R^2$ is selected from methyl, ethyl, propyl and butyl and $R^3$ is selected from an unsaturated $C_{1-5}$ alkyl.

7. A process according to paragraph 6 wherein $R^2$ is $CH_3$ and $R^3$ is $=CH_2$.

8. A process according to any one of the preceding paragraphs wherein X is H, Y is H, Z is H, n=0, $R^1$ is a group of formula III, in which $R^2$ is $CH_3$ and $R^3$ is $=CH_2$.

9. A process according to any one of the preceding paragraphs comprising providing means for containing the immobilised acid, contacting the immobilised acid with the compound of formula II and passing a gas through the immobilised acid.

10. A process according to paragraph 9 wherein the gas is air.

11. A process according to paragraph 9 or 10 wherein the immobilised acid is contacted with the compound of formula II in the absence of an organic solvent.

12. A process according to any one of the preceding paragraphs step (i) is performed in the presence of water.

13. A process according to any one of paragraphs 9 to 12 wherein the means for containing the immobilised acid comprises a fluidised bed reactor.

14. A process according to any one of paragraphs 9 to 13 wherein the process comprises extracting the gas from the means for containing the immobilised acid after the gas has passed through the immobilised acid.

15. A process according to any one of the preceding paragraphs wherein the process further comprises the step of polymerising the polymerisable monomer of formula 1.

16. A process according to paragraph 15 wherein acid formed during the process is not neutralised prior to polymerisation.

17. A process according to paragraph 15 wherein the process is under conditions to have cross-linker formation and/or acid such as a majority of acid, or an amount of acid so as to promote cross-linker formation, or any acid, present in the polymerisable composition is neutralised prior to polymerisation and/or that any neutralisation of acid present in the polymerisable composition is appreciable or is to an extent such that there is cross-linker formation as compared with an absence of any neutralisation and/or acid present with formula I resulting from the process is separated or completely separated or neutralised or completely neutralised or may be removed, e.g., at least to an extent to promote cross-linker formation.

18. A process according to paragraph 16 or 17 wherein the acid is selected from methacrylic acid and acrylic acid.

19. A process according to paragraph 15, 16, 17, or 18 further comprising forming an ocular device from the polymer.

20. A polymerisable monomer, polymer or composition obtainable in accordance with process as defined in any one of paragraphs 1 to 19.

21. A polymerisable monomer, polymer or composition obtained in accordance with a process as defined in any one of paragraphs 1 to 19.

22. An ocular device prepared in accordance with a process as defined in any one of paragraphs 1 to 19; optionally including forming the polymerisable monomer, polymer or composition obtained from the process into the ocular device and/or polymerising the monomer obtained from the process, optionally with neutralisation of acid present with the monomer resulting from the process, and forming the product therefrom into the ocular device.

23. An ocular device prepared from the polymerisable monomer, polymer or composition obtainable from any one of paragraphs 19 to 20; optionally including forming the polymerisable monomer, polymer or composition obtained from the process into the ocular device.

24. An ocular device prepared from the process of paragraphs 20 or 21.

What is claimed is:

1. A process for the preparation of a polymerizable composition comprising polymerizable monomer of formula I:

said process comprising the steps of:
(i) contacting a compound of formula II with an immobilized acid to thereby form a composition comprising the monomer of formula (I) and an acid by-product thereof,
wherein
X, Y, Z, P, and Q are independently selected from a hydrocarbyl group or hydrogen,
A is $(CH_2)_n$, wherein n is 0 or 1;
$R^1$ corresponds to either formula IIIA or formula IIIB where $R^2$ is selected from the group consisting of H, methyl, ethyl, propyl, and butyl, and
and
$R_3$ is an unsaturated $C_{2-5}$ alkyl; and
(ii) neutralizing the composition of step (i) with an immobilized hydroxide, to thereby provide a composition comprising the monomer of formula I and a cross-linker.

2. A process according to claim 1 wherein the immobilized acid is a strong acid.

3. A process according to claim 1 wherein the acid is immobilized on an ion exchange resin.

4. A process according to claim 1 wherein X and Y are independently selected from hydrocarbon groups having from 1 to 20 carbon atoms and hydrogen.

5. A process according to claim 1 wherein R1 corresponds to formula IIIA, and $R_2$ is $CH_3$.

6. A process according to claim 1 wherein X is H; Y is H, Z is H, n=0, $R^1$ corresponds to formula IIIA, and $R_2$ is $CH_3$.

7. A process according to claim 6 wherein prior to said contacting, the immobilized acid is contained, and after said contacting, passing a gas through the contained immobilized acid.

8. A process according to claim 7 wherein the gas is air.

9. A process according to claim 7 wherein the immobilized acid is contacted with the compound of formula II in the absence of an organic solvent.

10. A process according to claim 1 wherein said contacting is performed in the presence of water.

11. A process according to claim 7, wherein prior to said contacting, the immobilized acid is contained in a fluidized bed reactor.

12. A process according to claim 7, further comprising after said passing step, extracting the gas from the contained immobilized acid.

13. A process according to claim 1, further comprising, after said neutralizing, polymerizing the composition formed in step (ii), to thereby form a polymer.

14. A process according to claim 1, wherein said acid by-product formed in step (i) is methacrylic acid.

15. A process according to claim 1, wherein said acid by-product formed in step (i) is acrylic acid.

16. A process according to claim 13, further comprising forming the polymer formed in said polymerizing step into an ocular device.

17. A polymerizable monomer or composition formed by the process of claim 1.

18. A polymer formed by the process of claim 13.

19. An ocular device comprising the polymer formed by the process of claim 13.

20. A process for the preparation of a polymerizable composition comprising a polymerizable monomer of formula I:

said process comprising the steps of:
(i) contacting a compound of formula II with an immobilized acid having a $pK_a$ of less than 3 to thereby form a composition comprising the monomer of formula (I) and an acid by-product thereof,
wherein
X and Y are independently selected from hydrocarbon groups having 1 to 20 carbon atoms and hydrogen,
Z, P, and Q are independently selected from a hydrocarbyl group or hydrogen, A is $(CH_2)_n$, wherein n is 0 or 1;
$R^1$ corresponds to either formula IIIA or formula IIIB -continued

IIIB where R2 is selected from the group consisting of H, methyl, ethyl, propyl, and butyl, and
R$_3$ is an unsaturated C$_{2-5}$ alkyl; and
(ii) neutralizing the composition of step (i) with an immobilized hydroxide, to thereby provide a composition comprising the monomer of formula I and a cross-linker.

21. The process of claim 1, effective to form a composition comprising said monomer of formula (I) and about 0.50 percent or less of said cross-linker.

22. The process of claim 7, wherein said contacting results in formation of P—C(O)-Q, and said passing step is effective to remove said P—C(O)-Q from said composition.

23. The process of claim 22, wherein said process is effective to provide essentially quantitative conversion of the compound of formula (II) to the monomer of formula (I).

24. The process of claim 13, wherein the resulting polymer comprises 5% or less of a polymer formed by polymerization of said cross-linker.

25. The process of claim 3, wherein prior to said neutralizing, said immobilized acid is removed by filtration.

26. The process of claim 1, wherein the polymerizable monomer of formula (I) is glycerine methacrylate (GMA), the compound of formula (II) is 2,2-dimethyl-1,3-dioxolan-4-yl methyl methacrylate (GMAK), the acid by-product is methacrylic acid (MA), and the cross-linker is glycerol dimethacrylate.

* * * * *

UNITED STATES PATENT AND TRADEMARK OFFICE
CERTIFICATE OF CORRECTION

PATENT NO. : 7,645,846 B2
APPLICATION NO. : 09/977880
DATED : January 12, 2010
INVENTOR(S) : Holdstock et al.

It is certified that error appears in the above-identified patent and that said Letters Patent is hereby corrected as shown below:

Claim 5, column 15, line 59, "wherein R1 corresponds" should read --wherein $R^1$ corresponds--

Claim 7, column 15, line 63, "according to claim 6" should read --according to claim 1--

Claim 20, column 16, line 52, "a $pK_{a\ of\ less\ than}$ 3" should read --a $pK_a$ of less than 3--

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,645,846 B2  Page 1 of 1
APPLICATION NO. : 09/977880
DATED : January 12, 2010
INVENTOR(S) : Holdstock et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1355 days.

Signed and Sealed this

Sixteenth Day of November, 2010

David J. Kappos
*Director of the United States Patent and Trademark Office*